United States Patent [19]

Mueller et al.

[11] Patent Number: 4,588,850

[45] Date of Patent: May 13, 1986

[54] PROCESS FOR THE PRODUCTION OF ACETYLENE AND SYNTHESIS OR REDUCTION GAS FROM COAL IN AN ELECTRIC ARC PROCESS

[75] Inventors: Richard Mueller, Marl; Lothar Kerker, Dülmen; Cornelius Peuckert, Dinslaken, all of Fed. Rep. of Germany

[73] Assignee: Huels Aktiengesellschaft, Marl, Fed. Rep. of Germany

[21] Appl. No.: 644,420

[22] Filed: Aug. 27, 1984

[30] Foreign Application Priority Data

Aug. 26, 1983 [DE] Fed. Rep. of Germany ....... 3330750

[51] Int. Cl.$^4$ .......................... C07C 4/02; C07C 5/35
[52] U.S. Cl. .................................... 585/539; 48/202; 48/210; 252/373; 585/537
[58] Field of Search ............... 48/202, 210; 252/373; 585/539, 537

[56] References Cited

U.S. PATENT DOCUMENTS

| 4,367,363 | 1/1983 | Katz et al. ............................ 585/539 |
| 4,378,232 | 3/1983 | Peukert et al. ...................... 585/809 |
| 4,469,488 | 9/1984 | Calderon ............................. 48/210 |
| 4,472,172 | 9/1984 | Sheer et al. ......................... 48/210 |

FOREIGN PATENT DOCUMENTS 1059065  7/1979  Canada .

OTHER PUBLICATIONS

Hanson, "Carbon", vol. 16, 159–162 (1978).
Herlitz et al, Plasma Technology for Production of Synthesis Gas from Coal or Other Fuels, Seminar on Chemicals from Synthesis Gas, ECI, 14.06.83.

*Primary Examiner*—John Doll
*Assistant Examiner*—A. Pal
*Attorney, Agent, or Firm*—Millen & White

[57] ABSTRACT

For the manufacture of acetylene and synthesis or reduction gas from coal by means of an electric arc or plasma process, coal converted into powder form is pyrolyzed in an electric arc reactor with an energy density of 1 to 5 kWh/Nm$^3$, a residence period of 0.5 to 10 msec and at a temperature of at least 1500° C. such that the gaseous compounds derived from the coal do not exceed 1.8 times the so-called volatile content of the coal. The coke remaining after subsequent quenching is then fed to a second electric arc reactor in which the coke, by means of a gasifying medium in conjunction with heating by means of an electric arc or plasma process, is converted into synthesis or reduction gas furing a residence period of 1 to 15 sec and at a temperature of at least 800° C. The gas flow from the pyrolysis zone is cleaned and acetylene is recovered therefrom by selective solvents. The gas from the cleaning stage is similarly cooled and cleaned.

18 Claims, 1 Drawing Figure

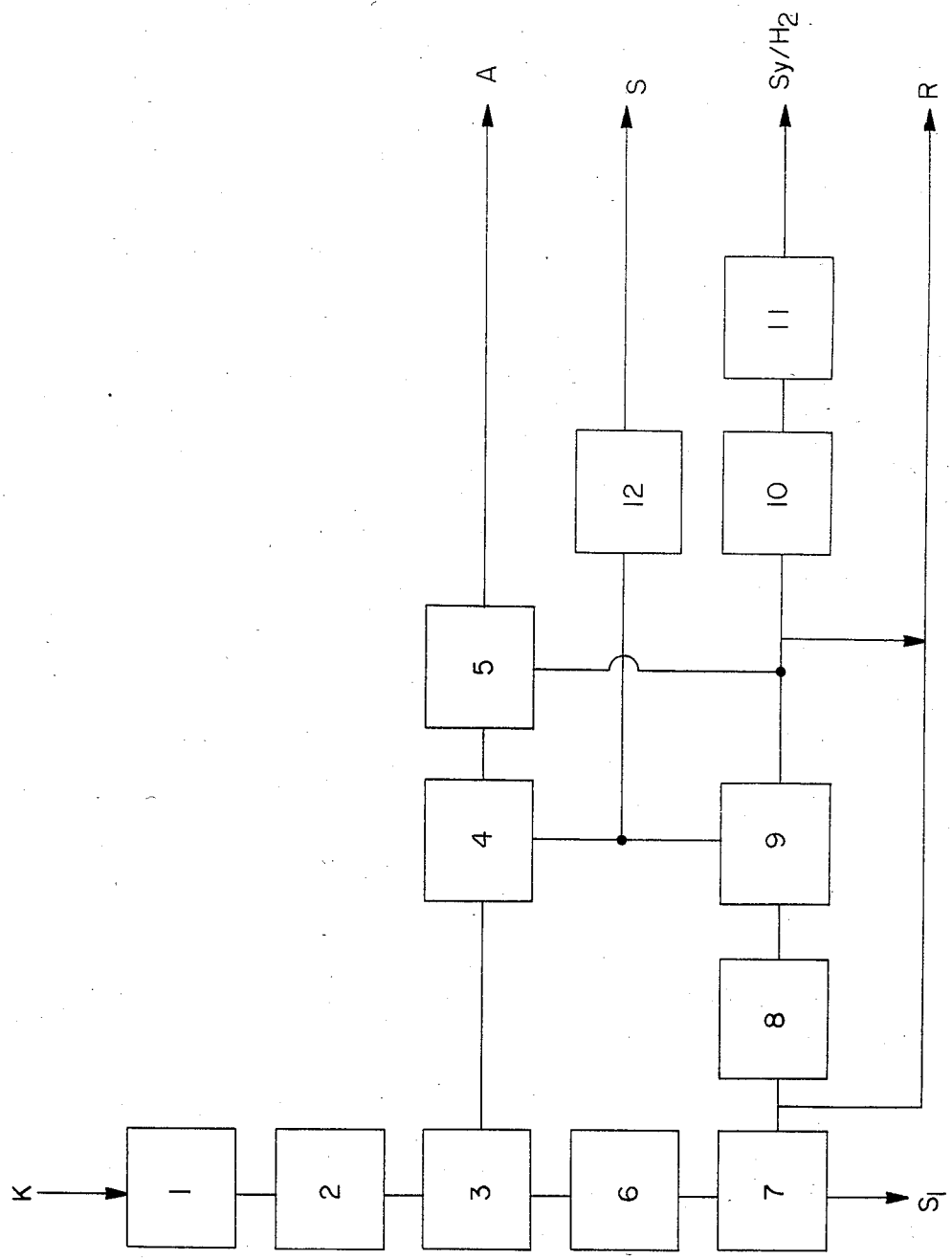

PROCESS FOR THE PRODUCTION OF ACETYLENE AND SYNTHESIS OR REDUCTION GAS FROM COAL IN AN ELECTRIC ARC PROCESS

BACKGROUND OF THE INVENTION

Considering that fossil raw materials are likely to become more scarce in the future, processes are gaining interest which make possible the utilization of electrical energy in energy-consuming processes which electrical energy can be generated on a non-fossil basis, e.g., nuclear energy or renewable resources such as hydrodynamic power and solar energy. If such energy is required at high temperatures, electric arc or plasma processes are particularly suitable. Thus, the production of acetylene from gaseous and liquid hydrocarbons has been known for years and is conducted on a commercial scale (Gladisch, Hydrocarbon processing, Petroleum Refiner 41, No. 6, 159 to 164 (1962)). In that process, only about 50% of the fossil raw material requirements are saved as compared with processes based entirely on fossil materials, such as for example partial oxidation. In recent years, development work has commenced with a view to also producing acetylene from coal in an electric arc or plasma process (D. Bittner, H. Baumann, C. Peuckert, J. Klein, H. Jüntgen, Erdöl und Kohle Erdgas-Petrochemie 34, issue 6, 237 to 242 (1981)).

A further reaction in which plasma processes have been applied is the reforming of hydrocarbons or coal by means of a gasification medium such as steam or carbon dioxide to form a gas mixture composed predominantly of CO and $H_2$. The latter finds wide technical use in the chemical industry as synthesis gas or in the metallurgical industry as reduction gas. Here, as well, the employment of the electric arc process permits a savings of about 50% of the direct fossil energy requirements.

In the pyrolysis of coal in the plasma process it is possible to derive substantially larger amounts of volatile matter from the coal than in conventional coking processes. A yardstick for the proportion of compounds which may ordinarily be recovered is the content of so-called "volatiles" of the coal which is determined under standardized assay conditions (DIN 51 720 or ISO 562).

In plasma pyrolysis, a yield of volatile compounds can be recovered exceeding by a factor of approximately 2 the "volatile" content of the coal. In that case these volatiles are composed predominantly of $C_2H_2$ and CO. Coke is left behind as a residue. However, in large scale practice there are obtained some 1 to 2t of coke/t $C_2H_2$. This must be disposed of. If this coke is combusted in a power plant, this permits about 50% of the electrical energy requirements for the acetylene production to be generated—being in the region of 10 kWh/kg $C_2H_2$. However, as a result, a major part of the advantage of an electric arc process is lost, i.e., the co-use of electrical energy on a non-fossil basis.

SUMMARY OF THE INVENTION

Accordingly, it is an object of this invention to provide a potential use for the coke obtained in a plant for acetylene production from coal in an electric arc or plasma process, which process is readily suitable for integration into a chemical plant and permits an optimal combined use of electrical energy from various sources, more particularly including that generated on a non-fossil fuel basis.

It is another object of this invention to provide such a combined process which results.

Upon further study of the specification and appended claims, further objects and advantages of this invention will become apparent to those skilled in the art.

These objects have been attained according to this invention by providing a process for the manufacture of acetylene and synthesis or reduction gas from coal by means of an electric arc or plasma process, wherein coal provided in powder form is so pyrolized in a first electric arc reactor at an energy density of 1 to 5 $kWh/Nm^3$, a residence period of 0.5 to 10 msec and a temperature of at least 1500° C., that the gaseous compounds obtained from the coal do not exceed 1.8 times the so-called "volatile" content of the coal; the coke remaining after quenching is passed to a second electric arc reactor in which the coke is converted into synthesis or reduction gas by means of a gasifying medium and heat in an electric arc or plasma process, wherein there is maintained a residence period of 1 to 15 sec and a temperature of at least 800° C.; the gases obtained in the pyrolysis and gasification stage being processed in a known manner, e.g., in that the gas flow from the pyrolysis zone is cleaned and acetylene is recovered therefrom by means of selective solvents; and the gas from the gasification stage is cleaned, optionally after cooling.

BRIEF DESCRIPTION OF THE DRAWING

Various other objects, features and attendant advantages of the present invention will be more fully appreciated as the same becomes better understood when considered in conjunction with the accompanying drawing.

The FIGURE schematically illustrates one method of conducting the process of this invention.

DETAILED DISCUSSION

Coal which has been prepared in fine powder form, e.g., as is customary for coal dust burners (90% below 100 μm), is first employed to produce acetylene in a first stage in an electric arc or plasma process at a residence period of 0.5 to 10 msec, preferably of 1.0 to 2 msec and temperatures of at least 1500° C., preferably of 1500° to 3000° C. The coke formed thereby is separated and converted in a second stage into a reduction or synthesis gas by applying an electric arc process with a gasification medium at a temperature of at least 800° C., preferably of 800° to 1700° C. and a residence period of 1 to 15 sec, preferably of 2 to 6 sec.

There exists a prejudice against such processes due to the known fact that even coke produced at lower temperatures has a gasification rate which is substantially less than that of coal due to its low volatile content, and also due to the "sintering" of the carbon skeleton at the coking temperature of 900° to 1200° C.

Thus, e.g., Herlitz and S. Santen (Plasma technology for production of syntehsis gas from coal and other fuels, Seminar on Chemicals from Synthesis Gas, ECI, 14.06.83) describe an electric arc process for coal gasification, in which in a shaft furnace coke is added to the coal, the coke conversion rate being only 7 to 10% of that of the coal conversion.

Bearing in mind that in the acetylene production from coal in the electric arc process, the reaction is conducted at substantially higher temperatures exceeding 1500° C., there existed little prospect that the coke derived from the electric arc, plasma pyrolysis could be gasified in technically feasible residence periods, on the order of seconds, in a subsequent electric arc process.

It has now been found, surprisingly, that these contemplated disadvantages can be avoided if the pyrolysis reaction is conducted in a first stage at an energy density of 1 to 5 kWh/Nm$^3$, a temperature of at least 1500° C. and a residence period of 0.5 to 10 msec in such a manner that the yield of gaseous compounds does not exceed 1.8 times the so-called "volatile" content of the coal, preferably from 1.1 to 1.8 times it. One embodiment of the process of this invention will be described in more detail with reference to the FIGURE.

Ground, powdered and dried coal (particle size 90% less than 100 μm; (K)) is injected by means of a propellent gas containing at the most traces of oxidizing components for example a propellent gas of hydrogen, CO, CH$_4$ or other gaseous hydrocarbons, into an electric arc reactor 1 which may be operated either in a single stage or a dual stage manner. Where the reactor is of the single stage type, the coal is heated up directly with the propellent gas by the electric arc, whereas in a dual stage reactor the energy is first transmitted to a plasma gas and the coal is injected in the second stage jointly with the propellent gas into the hot plasma jet. In principle, any coal is suitable for use.

Suitable for use as plasma gas, when used, are H$_2$, CO, hydrocarbons such as CH$_4$ and other saturated and unsaturated hydrocarbons and N$_2$ as well as mixtures of the foregoing.

The reaction conditions in the electric arc reactor are routinely so selected that the yield of gaseous compounds is not more than 1.8 times the volatile content. The conditions required to achieve this characteristic can be set up in numerous ways with which the person skilled in the art is familiar. For example, according to the thesis of C. Peuckert (Aachen 1980), the energy density of the plasma jet may be increased to 1 to 5 kWh/Nm$^3$, preferably 2.0 to 3.5 kWh/Nm$^3$ so as to increase the temperature thereof to at least 1500° C., preferably 1500° to 3000° C. in order to increase the output of volatiles from the coal. Other expedients which will be apparent to the person skilled in the art include increasing the energy supply based on the coal feed, for example to 1.0 to 5 kWh/kg coal, increasing the residence time from 0.1 to 10 msec, preferably 0.5 to 5 msec, or lowering the pressure from 1.3 to 0.1 bar, a lower energy density and temperature being preferred if the residence period is relatively long. After proceeding through the reaction zone, the reaction medium is interrupted by a direct or indirect quenching process 2 e.g., with water, liquid gas or a heat exchanger such as a waste heat boiler with steam generation or a suitable combination of these.

After this temperature reduction, for example to 150° to 300° C., the coke is separated 3 and the cracking gas, which, inter alia, comprises C$_2$H$_2$, H$_2$, CO and volatile S compounds such as H$_2$S and CS$_2$ is passed on to further processing for the recovery of acetylene (A) in 4 and 5, e.g., according to the process of DE-OS 31 50 340 (=U.S. Pat. No. 4,367,363, whose disclosure is incorporated by reference herein). The acetylene is recovered from the gas flow conventionally, e.g., by means of selective solvents. Suitable conventional solvents include for example water, methanol, N-methylpyrrolidone or mixtures thereof.

The carbon disulphide produced in the pyrolysis zone and recovered as a mixture of other gases in the first gas cleaning stage 4 and 5 is preferably fed to the gasification zone 6. The sulphuretted hydrogen formed in the pyrolysis may be conventionally converted to sulphur (S) jointly with the sulphuretted hydrogen derived from the gasification step, for example in a Claus plant, e.g., as shown in the FIGURE by the line to 12.

The coke is conventionally introduced into a further electric arc reactor 6, e.g., by means of suitable conveyor means, for example worm conveyors, or by means of a propellent gas and/or a gasification medium, which here may also contain oxidizing components such as H$_2$O or CO$_2$, or after slurrying with water. Suitable plasma gases include H$_2$, CO, H$_2$O and/or CO$_2$. It is preferred to employ as all or part of the plasma gas, a gasifying medium such as steam, carbon dioxide or mixtures of these. Preferably, the molar O/C ratio will be from 1.1 to 1.5, in particular 1.1 to 1.2.

This second electric arc reactor may similarly be designed in single or dual stage form. In the dual stage form, such as described in DE-OS No. 31 04 281 (=U.S. Pat. No. 4,362,554, whose disclosure is incorporated by reference herein), the plasma jet may e.g. be composed of hydrogen, a recycle gas from other processes, for example a CO/H$_2$ mixture or a gasifying medium, such as e.g. steam.

After a residence period of 1 to 15 sec, preferably 2 to 6 sec, at temperatures of at least 800° C., preferably 800° to 1700° C., in particular 1000° to 1500° C., the slag (S1) is separated 7. Depending on the intended purpose for finally using the gaseous products, the desired partial gas flow is branched off and the residual gas flow is cooled by way of a heat exchanger 8, in a manner known from various coal gasification processes using oxygen (B. Cornils, I. Hibbel, P. Ruprecht, R. Dürrfeld, J. Langhoff, Hydrocarbon Processing, page 152, Jan. 1981).

The gas is then freed of acid components such as CO$_2$ and H$_2$S in a manner known per se 9 and passed to further end use.

Such known uses include use as reduction gas (R) for use in direct reduction or in the blast furnace, and as synthesis gas (Sy) as is required for example for the Oxo synthesis, methanol synthesis or NH$_3$ synthesis, if necessary or desired, after a conventional converting step 10 and/or a gas separation 11. In this context, the CO/H$_2$ mixture derived from the acetylene purification 5 may be included advantageously in the processing stages 10 and 11 in order to be similarly put to suitable use. Because part of the S compounds of coal are already converted into H$_2$S during the pyrolysis step, the corresponding gas flows derived from the pyrolysis and the gasification stages can be passed to a joint S recovery plant 12, for example a Claus plant.

Unless indicated otherwise herein, all processes and steps described above are per se conventional, e.g., as disclosed in Hydrocarbon Processing, April 1982, p. 85, which disclosures are incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

COMPARATIVE EXAMPLE A

In an electric arc furnace operated with a capacity of 360 kW and with $H_2$ as the plasma gas at a pressure of 1 bar, finely gound and dried coal (90% less than 100 μm) is injected (at a rate of 100 kg/h—based on moisture and ash-free coal (maf)—and with a volatile content, determined according to DIN 51 720 of 30% maf) by a hydrogen flow with a coal loading of 10 kg/kg hydrogen into the plasma jet emerging from this electric arc furnace. The latter has an energy density of 4.0 kWh/Nm$^3$. The coal is heated up and pyrolized in a cylindrical reactor at a mean temperature of 2600° C. during a residence period of 13 milliseconds. The gas-coke mixture is cooled to 200° C. by the injection of water. The coke is separated in a cyclone. The gas is cleaned in a known manner by water and alkali scrubbing. The gas flow rate is determined by a measuring orifice and by density measuring and amounts to 78.5 kg/h. After subtraction of the amounts of gas introduced, this leaves a gas yield derived from the coal of 60 kg/h. Accordingly, 60% of the coal has been converted during the pyrolysis into volatile components, corresponding to twice its volatile content. The acetylene yield amounts to 27%. The specific energy requirement which is important for the economics of the process, is 13.3 kWh/kg $C_2H_2$.

The coke is then injected into the head of a brick lined cylindrical reactor by means of a mixture of 25% $H_2O$ and 75% $H_2$ in an amount of 60 kg/h, based on water and ash-free coal, at a temperature of 150° C. Simultaneously, a plasma jet of hydrogen with an energy density of 3.0 kWh/Nm$^3$, similarly generated in an electric arc reactor with a capacity of 300 kW, also flows into the reactor. In addition, steam is introduced at the head of the reactor such that, based on the carbon content of the coke, a molar O/C ratio of 1.15 is maintained.

The reactor is so dimensioned that the average residence period of the gas amounts to 6 sec. The temperature of the product gas is 1300° C. Part of the slag collects in liquid form at the bottom of the reactor while the gas is withdrawn sideways at the end of the reactor. The slag flows through a heat exchanger and is then cooled down to 30° C. by means of a venturi scrubber. At the same time, soot is scrubbed out such that, in the discharged gas, carbon cannot be detected. A sample is taken from the effluent water and the solid carbon content is determined. From the amount of water and the C content, it is possible to calculate a degree of gasification of 70%, i.e., the degree of gasification of the coke is too low for a technically feasible process.

The yield of synthesis or reaction gas $(CO+H_2)$ amounts to 2.6 Nm$^3$/kg of coke.

EXAMPLE 1

The design of the plant and the reaction conditions correspond to those in Comparative Example A except that the residence time in the pyrolysis zone is reduced from 13 to 2 msec. The amount of gas is now increased by only 45 kg, i.e., 1.5 times the volatile content of the coal. The acetylene yield now amounts to 32% and the specific energy requirement amounts to 11.3 kWh/kg $C_2H_2$. The same amount of coke as in Comparative Example A is now fed into the second reactor under the same operating conditions. From the C determination and the amount of water, there is determined a degree of gasification of the coke of 97%, as is normal for a technical scale coal gasification process. The yield in respect of synthesis or reduction gas amounts to 3.6 Nm$^3$/kg of coke. The gas processing in both stages proceeds in the known manner.

EXAMPLE 2

In a single stage electric arc furnace of 360 kW operated with a mixture of 80% $H_2$, 19% CO derived from the gasification stage and 1% $CH_4$ serving as a plasma gas having an energy density of 2.8 kWh/Nm$^3$ and a pressure of 0.5 bar, finely ground coal having a volatile content of 25% is injected at a rate of 120 kg/h, based on water and ash-free coal, with a gas of the same composition as the plasma gas. It is pyrolized at 2200° C.

After a residence period of 2 msec, the gas is cooled first by water quenching to 600° C. and then with a waste heat boiler to 200° C., coke and gas being separated as in Comparative Example A. The gas yield amounts to 42%, i.e., 1.68 times the volatile content of the coal. The acetylene yield amounts to 27%, the specific energy requirement being 11.1 kWh/kg $C_2H_2$. The same amounts of coke as in Comparative Example A are now fed to the second electric arc reactor under the same operating conditions. From the C determination and the amount of effluent water, a degree of gasification of 92% is determined. The yield of synthesis gas amounts to 3.4 Nm$^3$kg. Gas processing in both stages proceeds in a known manner.

EXAMPLE 3

Coke produced as in Example 1 is fed at a rate of 60 kg/h by means of a gas mixture according to Comparative Example A into the reactor, also according to Comparative Example A. A plasma jet generated in an electric arc reactor having a capacity of 300 kW from a gas mixture composed of 60 volume % $H_2$, 25 volume % $H_2O$, 10 volume % $CO_2$ and 5 volume % CO, flows into this reactor, again as in Comparative Example A. The energy density amounts to 3.2 kWh/Nm$^3$ of the gas mixture. In addition, as in Comparative Example A, steam is introduced such that the overall ratio of O/C amounts to 1.2. The residence period of the gas amounts to 5 sec and the temperature of the product gas is 1350° C. The remaining conditions and the gas processing are conducted as in Comparative Example A. A degree of gasification of 95% is attained, corresponding to a yield of synthesis or reduction gas of 3.5 Nm$^3$/kg of coke.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the manufacture of acetylene and a synthesis or reduction gas based on hydrogen and carbon monoxide, comprising pyrolyzing powdered coal in a first electric arc-plasma reactor operating at an energy density of 1 to 5 kWh/Nm$^3$, with a residence period of 0.5 to 10 msec and at a temperature of at least 1500° C., whereby the amount of the resultant gaseous compounds obtained from the coal in the pyrolysis reaction does not exceed 1.8 times the volatile content of the coal;

passing quenched coke remaining after the pyrolysis step into a second electric arc-plasma reactor in which the coke is converted into said synthesis or reduction gas by means of a gasifying medium, under a residence time of 1 to 15 sec and a temperature of at least 800° C.;

the gas obtained in the pyrolysis stage containing acetylene and the gas obtained in the gasification stage containing $H_2$ and CO and constituting a synthesis or reduction gas.

2. A process of claim 1 further comprising treating the gases obtained in the pyrolysis stage to separate acetylene therefrom and recovering acetylene.

3. A process of claim 1 further comprising treating the gases obtained from the gasification stage to separate a mixture of $H_2$ and CO therefrom, and recovering said mixture as synthesis or reduction gas.

4. A process of claim 2 further comprising treating the gases obtained from the gasification stage to separate a mixture of $H_2$ and CO therefrom, and recovering said mixture as synthesis or reduction gas.

5. A process of claim 4 wherein the acetylene is recovered by treating the pyrolysis gas product stream with solvents selective to the acetylene.

6. A process of claim 1 wherein the mean temperature in the pyrolysis zone is 1500° to 3000° C. and that in the gasification zone is 800° to 1700° C.

7. A process of claim 4 wherein the product gas from the pyrolysis stage, after the separation of the acetylene, contains $CO/H_2$ and is introduced into the gaseous product from the gasification stage.

8. A process of claim 4 wherein the gases remaining after said acetylene recovery and said recovery of a mixture of CO and $H_2$ contain $H_2S$, and these two gas streams are combined and then treated to yield sulfur.

9. A process of claim 2 wherein carbon disulfide is contained in the gaseous product in the pyrolysis zone or is contained in a gas obtained in the treatment used to separate acetylene therefrom, and one or both of these carbon disulfide-containing gases are fed to the gasification zone.

10. A process of claim 1 wherein the electric arc furnace used in the gasification stage is operated using a plasma gas composed wholly or partially of a gasification medium comprising steam, carbon dioxide or a mixture thereof.

11. A process of claim 4 wherein the electric arc furnace used in the gasification stage is operated using a plasma gas composed wholly or partially of a gasification mexium comprising steam, carbon dioxide or a mixture thereof.

12. A process of claim 11 wherein cooling stages are employed in the process to treat the gas streams and wherein steam is contained in the gasifying medium and is obtained from one of the heat exchangers used in the cooling stages.

13. A process of claim 11 wherein said gas treating stages produce a carbon dioxide containing gas and carbon dioxide derived from said gas is used wholly or in part as the gasifying medium.

14. A process of claim 6 wherein the residence time in the pyrolysis stage is 1–2 msec and in the gasification stage is 2–6 sec.

15. A process of claim 4 wherein the particle size of 90% of the coal is less than 100 $\mu$m.

16. A process of claim 4 wherein the coke obtained after the pyrolysis stage is quenched to 150°–300° C.

17. A process of claim 4 wherein the $H_2$ and CO mixture obtained as a product is subsequently fed to a process wherein it is used as a synthesis gas.

18. A process of claim 4 wherein the $H_2$ and CO mixture obtained as a product is subsequently fed to a process wherein it is used as a reduction gas.

* * * * *